US005532164A

United States Patent [19]

Blanchette et al.

[11] Patent Number: 5,532,164

[45] Date of Patent: Jul. 2, 1996

[54] BIOLOGICAL CONTROL FOR WOOD PRODUCTS

[75] Inventors: Robert A. Blanchette, Shoreview, Minn.; Roberta L. Farrell, Groton, Mass.; Chad J. Behrendt, St. Paul, Minn.

[73] Assignee: Sandoz Ltd., Basel, Switzerland

[21] Appl. No.: 247,131

[22] Filed: May 20, 1994

[51] Int. Cl.[6] .............................. D21C 5/00; D21C 9/08; C12N 1/14

[52] U.S. Cl. .......................... 435/277; 435/267; 435/278; 162/70; 162/161; 424/93.5

[58] Field of Search .................................... 435/277, 267, 435/274, 278; 162/DIG. 4, 70, 161; 424/93.5, DIG. 10

[56] References Cited

U.S. PATENT DOCUMENTS

| | | | |
|---|---|---|---|
| 4,648,988 | 3/1987 | Van Dijck et al. | 252/608 |
| 5,476,789 | 12/1995 | Farrell et al. | 435/267 |
| 5,476,790 | 12/1995 | Blanchette et al. | 435/277 |

OTHER PUBLICATIONS

Farrell et al. "Cantapip: a biopulping product for control of pitch and resin acid problems in pulp mills", J of Biotechnology, vol. 30 (1993) pp. 115–122.

Hiratsuka et al. "Potential for biological protection against blue Stain". Canadian J of Forest Research. vol. 24, Mar., (1994), pp. 174–179.

Croan et al. "Biological Control of the Blue Staim Fungus." Biosis Abs 91:500 392 from Master Org 24(4) (1990) pp. 256–266.

Wilhelmsen et al. "Damage of unbanked conferous sawlogs:" Caplus Abstract (1969):46386 from Medd. Non Skogfonsoesv (1968) 25(90) pp. 239–330.

Rättö et al., "Potential of enzymes of wood debarking," Tappi Journal, vol. 76, No. 2 (Feb. 1, 1993) pp. 125–128.

Y. Yazaki et al., "Extractive components responsible for the discoloration of Ilomba wood (Pycnanthus angolensis Exell)," Holz als Roh-und Werkstoff, vol. 43, No. 9 (Sep. 1985) pp. 359–363.

*Primary Examiner*—Esther M. Kepplinger
*Assistant Examiner*—Timothy J. Reardon
*Attorney, Agent, or Firm*—Robert S. Honor; Carl W. Battle; Michael P. Morris

[57] ABSTRACT

Fungi which grow white/colorless and reduce pitch are used to protect structural wood before or after cutting from logs against color staining by staining fungi.

13 Claims, No Drawings

BIOLOGICAL CONTROL FOR WOOD PRODUCTS

This invention relates to a method for biologically controlling the discoloring of wood products by fungi.

Harvested trees supply wood for two main uses. One is the use in making paper and cardboard in which tree wood is converted into pulp. The other is the use in making lumber and other solid wood shaped objects used in construction, furniture and the like, herein collectively "structural wood", in which processes the wood is not pulped or fiberized.

When trees are cut down for structural wood, they commonly become infected by any one or more of a variety of fungi which can stain the wood in any one or more of a variety of colors. A major problem in the lumber industry today involves loss of value in lumber products due to the unsightly staining caused by blue stain fungi which can color the wood gray, dark blue and black, such staining :appearing in the wood even though the outer surfaces or regions of the wood have been cut away in forming the lumber.

In recent years there has been active research in the area of the potential use of fungi and their enzymes in the pulp and paper industry, based mainly on the ability of fungi to decay wood. A major aspect of this work has been directed to fungi and particularly enzyme systems which would remove lignin. One success in this research involved the discovery that certain xylanases could be used to remove lignin and assist in bleaching pulps. The idea of "biopulping" or the concept that certain fungi could be applied to wood chips to advance the process of primary lignin removal (pulping itself) has proved less successful.

However, certain of the instant inventors working with others discovered that certain fungi which in fact normally stain wood could be used to remove pitch from wood forms to be used in making pulp, see published European patent application No. 0387187A2. It was then found that such pitch-degrading fungi could be converted to white or colorless growing fungi which retained their good pitch-degrading properties, thus eliminating the drawback inherent when pulpwood is stained, see published European Patent Application No. 0470929A2.

Subsequent improvements in the preferred pitch-degrading fungi of the genus Ophiostoma were later disclosed in U.S. application Ser. No. 899,796, filed Jun. 17, 1992 which is the parent application to U.S. application Ser. No. 138,174, filed Oct. 15, 1993, both now abandoned, in turn a parent application to U.S. application Ser. No. 267,684, now pending, which described a white-colorless growing strain of *Ophiostoma Piliferum* which has been made commercially available under the registered trademark CARTAPIP®97. Subsequently, certain white rot fungi were also found to also be useful to reduce pitch, as disclosed in U.S. application Ser. No. 034,443, filed Mar. 19, 1993 now abandoned, which is the parent application to U.S. Pat. No. 5,476,690, the disclosure of which and said application Ser. No. 267,684, granddaughter application to 899,796 are incorporated herein by reference.

When pitch content is to be reduced in accord with the aforementioned technology, the pitch degrading fungus is preferably inoculated onto wood chips and allowed to grow, usually for from 4 to 30 days. When a white/colorless growing fungus is used for pitch degradation, it was reported that such fungi could improve the color of the treated chips and reduce bleaching requirement by reducing the apparent growth/amount of blue stain fungi which had naturally infected the wood. It was also disclosed that pitch could be reduced by inoculating the pitch-reducing fungi onto timber prior to chipping or other mechanical action in the process of forming pulp, such inoculation taking place at the end of the logs and/or by scoring the logs lengthwise and inoculating into the scores. However, the color effects of inoculating logs in such fashion on the later growth of naturally infecting staining fungi in the logs themselves was not studied or reported.

Fungi which have been described as useful for pitch degradation generally penetrate the wood, creating narrow voids and openings which appear related to other advantages observed in pulping wood treated with such fungi. However, such treatments have little or no effect on the cellulose, hemicellulose or lignin content of the wood.

It has now been found in accord with the present invention that the color staining of structural wood by color-staining fungi may be surprisingly suppressed to a great degree merely by inoculating both the cut end of timber logs with a fungus which grows white and/or colorless and which acts to reduce the pitch content of the wood.

Despite the fact that the aforementioned white/colorless growing pitch degrading fungi will deeply penetrate and leave voids where pitch has been removed, it has been found that such voids have substantially no adverse affect on the quality of structural lumber produced from logs treated with such fungi in accord with this invention. Because such previously disclosed pitch-degrading fungi are among the more virulent growing known to us, they generally constitute preferred fungi for use in the invention.

It is also within the scope of the invention to additionally protect the length of logs between the treated ends against the infestation or natural inoculation of staining fungi which could stain the wood portions between the ends. For example, in areas where bark beetles are present which can bore into logs and carry with them, as is known, spores or other inoculum of the staining fungus, the log lengths may be treated with an insecticide effective to suppress the bark beetles. Lengthwise areas which have been debarked in tree-falling or handling may also be inoculated with a white/colorless growing fungus. As an alternative or where inoculum of staining fungi are particularly high, the logs may be scored lengthwise, preferably at intervals of 8 to 20 inches around the log circumference, and the white/colorless growing fungus inoculated into the scoring which generally will be carried out to a depth sufficient to substantially reach the under-the-bark wood. If and when logs are to be debarked, and then stored, it is within the scope of the invention to treat the entire debarked surface with the white/colorless growing fungi to protect against staining fungi. Moreover, a considerable expense is encountered in the structural wood industry in protecting structural wood after cutting from logs against the color staining fungi which could infect the wood before or after cutting to form the structural wood, typically by spraying with an environmentally unsound fungicide such as pentachlorophenol. It is further within the scope of this invention to protect such structural wood against staining fungi by inoculating at least the lengthwise surfaces, or at least 60% of the surface area, preferably 80% and more, preferably all surfaces, of such wood with a pitch degrading fungus which grows white/colorless. The fungus is then allowed to grow on the structural wood which is maintained under environmental conditions sufficient to permit growth for at least about 14 days. Such inoculation desirably takes place no more than two weeks after the structural wood is cut from its log source, preferably in no more than one week, more preferably in no more than 4 days and most preferably in no more than 2 days. Such treatments are particularly useful to inhibit staining when the structural wood is stored and/or shipped for long periods in environments where staining fungi may be present, such as in ships or trucks which had previously carried infected wood forms such as logs, wood chips and the like.

The more preferred fungi for use in the invention are white/colorless growing fungi of the fungal classes Ascomycetes and Deuteromycetes as taught in the aforementioned published European Application No. 0470929A2 which contains a disclosure similar to U.S. application Ser. No. 657,581, filed Feb. 19, 1991, now abandoned, which is the parent application of U.S. Pat. No. 5,476,789, the disclosures of which being incorporated herein by reference. Such fungi involve a variety of genera which comprise genera classified in the sub-class Ophiostomatales as well as genera including the imperfect states associated to Ophiostomatales. Examples of such Ophiostomatales genera include without limitation Ceratocystis, Ceratocystiopsis, Graphium, Leptographium, Ophiostoma, Phialocephala and Sporothrix as defined with reference to the generic concepts stated in Harrington T.C., "New combinations in Ophiostoma or Ceratocystis species with Leptographium anamorphs", Mycotaxon, 1987, 28:39–43 and in "Leptographium Species, Their Distributions, Hosts and Insect Vectors", Harrington T. C. & Cobb F. W., 1988, pages 1–39, APS press, St. Paul, Minn., as well as Rhinocladiella and Hyalodendron as defined with reference to Hawksworth et al. "Ainsworth and Bisby's Dictionary of Fungi", 1983, 7th Edition, Commonwealth Mycological Institute, Kew, Surrey, England. Other Examples of genera (not classified as Ophiostomatales) in which penetrating fungi are found on a limited species basis include Alternaria, Cadophora, Chloridium, Diplodia, Dactylella, Fusarium, Hormodendron, Hormonema, Phialophora, Sphaeropsis, Trichosporium, Codinaea and Valsa as defined with reference to Hawksworth, et al. (supra). Preferred fungi are found in the genera Chloridium, Dactylella, Phialophora and Valsa as well as in the genera classified as Ophiostomatales, these latter genera being particularly preferred. More preferably, the fungi are found in the genera Ceratocystiopsis, Graphium, Leptographium and Ophiostoma, this latter being mostly preferred.

Preferred species of Ophiostoma include without limitation *Ophiostoma piliferum* and *Ophiostoma piceae,* particularly *Ophiostoma piliferum.* The pitch degrading fungi of Ascomycetes and Deuteromycetes are particularly preferred because they can grow on and into wood over long periods of time without substantially affecting or degrading the cellulose, hemicellulose or lignin content of the wood.

The Basidiomycetes including particularly the white rot fungi which degrade pitch in wood are also particularly useful since the action of the fungi in degrading pitch avoids metabolic states in which cellulose, hemicellulose and lignin may be attacked, hence allowing such Basidiomycetes fungi to protect against staining fungi over adequate periods of time without adversely affecting the quality of wood as structural wood. White rot fungi which degrade pitch and grow very well on non-sterile wood are *Schizophyllum commune, Trichaptum biforme, Phanerochaete gigantea* and *Phlebia tremellosa.*

Staining fungi protected against by the invention involve those which typically penetrate deeply into the wood and which themselves involve the fungal classes Ascomycetes and Deutermycetes, which staining fungi are typically represented by those also known as blue stains. Such fungi reduce pitch as is now known. While we do not wish to be bound by any theory concerning the invention, the beneficial results provided by the invention are probably due at least in part to the ability of the pitch-degrading white/colorless growing fungi to deprive the staining fungi of their primary food source.

In carrying out the invention is it important to inoculate the log ends soon after cutting down off the tree, the timing being influenced in part by the potential for infestation of staining fungi in the area. Desirably, the log ends will be inoculated in no more than two weeks after falling of the tree, preferably in no more than one week, more preferably in no more than 4 days and most preferably in no more than 2 days after cutting down of the tree. The particular fungus to be used will be selected in accord with guidelines given herein including growth ability on the particular wood type being treated. As is known, fungi grow to differing extents on different wood types, particularly when the wood is non-sterile. Hence, generally preferred fungi are those which grow well on the wood type of the substrate to be treated. Fungi more suitable for particular wood types are generally known from their history of natural growth habit on particular woods. Fungi of the genus Ophiostoma, for example, infect a variety of wood types and are very commonly found on pine and other woods such as oak, and are particularly preferred fungi for use in the invention. More particularly preferred species are *Ophiostoma piceae* and *Ophiostoma piliferum,* and particularly the latter. Especially preferred strains of *O. piliferum* which grow white and/or colorless with considerable growth strength or virulence on woods such as pine are those represented by the designation WZ58 when deposited with the NRRL on Jan. 24, 1991 with the Accession No. 18755 and by the designation WZ5803D97 when deposited with the NRRL on November 12, 1991 with the Accession No. 18917, said WZ5803D97 also being referred to herein as "D97" and also being represented by the product commercially available under the registered trademark CARTAPIP®97 from Sandoz Chemicals Corporation, Charlotte, N.C. Hence, particularly preferred are said WZ58 and D97 and derivatives, mutants and other white/colorless growing strains of *O. piliferum* which have at least the characteristics of growth virulence and pitch degradation exhibited by either on sterilized Southern Yellow Pine as described herein (and respectively in published European Patent Application No. 0470929A2 and U.S. patent application Ser. No. 889,796, filed Jun. 17, 1992, which is the parent application to U.S. application Ser. No. 138,174, filed Oct. 15, 1993, both now abandoned, in turn a parent application to U.S. application Ser. No. 267,684, now pending, the disclosure of both the European Application and the U.S. Application being incorporated herein by reference).

Any of the wide variety of wood types or genera processed by industry for structural woods may be treated in accord with the invention. These include both Gymnosperms and Angiosperms, and in particular both hardwoods and softwoods. Particular classes or types of wood therefore include without limitation conifers, pines, cedars, oak, maple, aspen, firs and birch. Softwoods such as pines generally have high pitch content and are readily colonized by pitch degrading fungi. Hence, they are more susceptible to invasion by pitch degrading staining fungi, but equally more easily treated in accord with the invention. Hardwoods, particularly those with low pitch contents, may in some instances require more thorough or high dose inoculum of the white/colorless growing fungi in order to ensure optimum germination.

The fungus to be used in the invention may be applied to the log and log ends in any of a variety of forms and ways. The fungus may be applied in any inoculum form giving rise to growth of the fungus, for example, in the form of mycelia or spores. Such inoculum may also be in liquid or dry form. For example, aqueous suspensions of mycelia and/or spores may be used, or the mycelia and/or spores may be dried or lyophilized to produce dry forms. Liquid aqueous forms of dilute or medium concentrations are generally preferred. Hence, the inoculum of the white/colorless growing fungus may be applied as a powder in dry form or sprayed or smeared by hand when in liquid form. The log ends will be completely covered with the inoculum such as by spraying the log ends to run off or smearing a medium concentrated liquid, e.g. of mycelia, over the entire log end (although pith and heartwood are seldom affected by staining fungi). When the fungus to be inoculated forms spores, a suitable inoculum involves, for example, relatively concentrated aqueous spore suspensions having from $10^5$ to $10^{10}$ CFU (colony forming units per milliliter, more usually $10^6$ to $10^9$ CFU/ml., although more or less concentrated forms may also be used. Similarly, the specific activity of mycelia in colony forming units (CFUs) may be determined by homogenizing the mycelia, e.g. for 5–10 minutes, and approximating the number of colonies resulting therefrom in a conventional manner when the fragments are grown on a nutrient substrate to determine the specific activity in CFUs for a given volume. Mycelia expressed as CFU will be used in similar activity concentrations to those of spores as given above. However, mycelia mats may also be simply dewatered and used as such as inoculum as demonstrated herein.

The fungal inoculum may be admixed with or applied concurrently with various adjuvants for various purposes. For example, an anti-transpirant (to inhibit desiccation) may be applied with the inoculum to ensure the suitable early growth conditions for the inoculum in cases of low humidity or high temperatures. Also, materials which act as stickers and/or nutrients may be used to ensure or sustain germination and provide a conducive environment for growth. Carboxymethylcellulose is preferred for these purposes, although a variety of materials may also be used.

DEPOSITS

We have under the Budapest Treaty deposited with the Northern Regional Research Center (NRRL) at Peoria, Illinois, U.S.A. the following fungi referred to herein, which deposits were assigned the Accession Numbers given below along with their date of deposit.

| Fungus | Accession No. | Deposit Date |
|---|---|---|
| *Schizophyllum commune* | NRRL 21056 | March 16, 1993 |
| *Trichaptum biforme* | NRRL 21055 | March 16, 1993 |
| *Phanerochaete gigantea* | NRRL 21054 | March 16, 1993 |
| *Phlebia tremellosa* | NRRL 21253 | May 16, 1994 |
| *Ophiostoma piliferum* (WZ58) | NRRL 18755 | January 24, 1991 |
| *Ophiostoma piliferum* (WZ5803D97) | NRRL 18917 | November 12, 1991 |

The foregoing deposits will be made available in connection with this application under the provisions of the Budapest Treaty and all rules of the United States Patent and Trademark Office, and will be resupplied if necessary in accord with such provisions and rules. It is noted that *Trichaptum biforme* has in the past also been referred to as *Polyporus pargamenus* and *Hirschioporus pargamenus,* see Gilbertson et al., "North American Polypores," Vol. 2, Fungiflore, Oslo, Norway 1987, pages 770–772 and Otjen et al., "Selective Delignification of Birch Wood (*Betula papyrifera*) by *Hirschioporus pargamenus* in the Field and Laboratory", Holzforschung 40 (1986), 183–189. Also, *Phanerochaete gigantea* has also been known in the past as *Peniophora gigantea,* see Burdsall, H. H., Jr., "A Contribution to the Taxonomy of the Genus Phanerochaete"., Mycological Memoir, No. 10, J. Cramer publishers, Braunschweig, Germany (1985).

As indicated, the white/colorless growing fungi to be used in the invention are those which will grow and reduce the pitch content of the wood to be protected. Those which are particularly good pitch degraders are generally preferred. The ability of a fungus to reduce pitch may be determined in various ways, but for purposes of this invention can be determined on sterilized woods samples in the form of wood chips by spraying the chips with a dilute aqueous inoculum of the fungus at a dosage of $10^{10}$ CFUs per kilogram of chips followed by accumulating the chips in a pile under laboratory conditions and allowing the fungus to grow on the chips at room temperature (20° C.) for 14 days. A control involving a water spray is also maintained. This method simulates the practical reduction of pitch as described in the above-referred to published patents. The terms "pitch" and "resin" with reference to wood are recognized to indicate extractable wood components of various types involving a complex mixture of hydrophobic substances including without limitation terpenes, the diterpene ("resin") acids, fatty acids and esters, glycerides, sterols and waxes and components associated therewith such as alcohols.

The pitch content of substrates is determined in accord with the standard TAPPI Procedure T204 OM-88 and may be expressed as mg. of pitch content per gram of substrates which had been extracted with DCM (a.k.a. methylene chloride). As used on a substrate such as wood chips, the treated chips are dried overnight at 60° C. and then ground into sawdust using a Thomas-Wiley Mill with a 10-mesh screen (10 gauge wire screen). Three (3) grams of dried sawdust are combined with about 30 ml. of DCM and the resulting mixture agitated overnight (about 15 hours) at room temperature. The liquid medium is pipetted from the mixture, filtered through a 0.45 micron organic filter, the liquid allowed to evaporate at room temperature overnight (for about 15 hours) in a preweighed dish and the residue oven-heated at 60° C. for 30 minutes to further remove DCM. The weight of the residue is determined in mg. as the pitch content and expressed either as mg. of pitch content per gram of substrate or as a percentage of pitch in original the substrate (% extractives). Pitch reduction is generally indicated when the inoculated fungus show a statistically significant reduction in pitch content compared with the control. Preferably, the pitch is reduced at least 10%, and more preferably at least 15% compared to the control.

The following examples are merely illustrative of the invention and its practice and are not intended to limit the same in any respect.

EXAMPLE I

Red pine trees, *Pinus resinosa,* approximately 15 to 20 years old, were felled at the Cloquet Forestry Center, Cloquet, Minn. The trees were cut into 30.5 cm sections and transported to the laboratory. Inoculation of random, unsterilized logs occurred one to three days after cutting.

Fungi used in the laboratory study consisted of a colorless strain of *O. piliferum,* herein D97, and three wild type blue stain fungi (*O. piliferum, O. piceae,* and O. minus). The blue stain fungi were obtained from Pinus species in the north Central United States. To inoculate logs, cultures were grown in 2% malt extract broth for 14 days prior to inoculation in order to allow fungal mat formation. A dewatered fungal mat was used to inoculate each log end. To determine the average weight of the mycelia inoculum, mats which were not used in inoculations were dried and weighed. Averaged dry mat weights were as follows; D97 0.105 g +/−0.009; *O. piliferum* 0.093 g +/−0.008; *O. piceae* 0.086 g +/−0.013; and *O. minus* 0.043 g/−0.002.

Treatments included inoculation with a) wild type blue stain fungi *O. piliferum, O. piceae* and *O. minus,* and colorless D97 alone; b) D97 inoculated simultaneously with each of the above other fungi; c) D97 inoculated two weeks after each of the other fungi; d) D97 inoculated two weeks before the other fungi; and e) D97 inoculated four weeks before the other fungi. A water inoculated control was also used. A total of 8 logs were used per treatment.

Log ends were inoculated by placing one fungal mat on each end of the red pine log. Fungal mats were evenly spread over the entire end of the log using a sterile glove pressed firmly enough to insure adherence. Simultaneous inoculation of two fungi involved mixing both mats by hand in a beaker, vortexing for 20 seconds, and placing them on the log end.

After inoculation, logs were stored at room temperature in clear plastic bags with two moist paper towels for 14 weeks. Every three weeks after inoculation the bags were opened to allow air exchange. Sampling and analysis of logs was carried out six and fourteen weeks after inoculation, with four logs sampled at each interval. Logs were flamed on both ends and split with a sterile ax. The right half of the log was used for isolations, with a set pattern which would allow identification of the colonization and distance of fungal growth. Isolation of fungi was performed aseptically, and three different media were used; a semi-selective medium for *basidiomycetes* modified slightly from that used by Worrall, "Media For Selective Isolation of Hymenomycetes", Mycologia 83, 296–302 (1991 ) (1.5% malt extract agar amended with 0.01 g/l streptomycin sulfate, 2 ml/1 lactic acid, and 0.06 g/l 50% WP benlate), Sabouraud Dextrose media with 0.40 g/l cycloheximide, 0.05 g/l chloramphenicol, and 0.05 g/l streptomycin sulfate (25), and 1.5% Difco Malt Extract and Difco Agar. After 1 or 2 weeks, fungal colonies growing on media were identified. Colonization percentages were determined by dividing the number of each fungal colony obtained by the total number of isolation attempts per log (average of 22 small chips), and represented samples taken at intervals up to a distance of 15.2 cm into the sapwood from the end.

Visual observations of D97 inoculated logs showed growth on log ends within 7 days, and dense mycelial growth over the entire cut surface 10 to 12 days after inoculation. The maximum distance colonized by D97 was 7.6 cm and 15.2 cm at 6 and 14 weeks, respectively; with an average growth of 6.8 mm per week. The percent sapwood colonized ranged up to 65% at 6 weeks and up to 66% at 14 weeks (Table 1). Colonization percentages at 6 and 14 weeks showed a decrease in the percent sapwood colonized, as the depth of the sampling interval from the end of the log increased (Table 1 ). Fourteen weeks after inoculation, 30% and 42% of the sapwood isolations yielded various Deuteromycete fungal at intervals of 1.3–2.5 cm and 1.3–5.1 cm, respectively.

TABLE 1

Percent of sapwood in inoculated treatments colonized by D97 at different intervals from the log end, at 6 and 14 weeks after inoculation in the laboratory trial:

TABLE 1

Percent of sapwood in inoculated treatments colonized by D97 at different intervals from the log end, at 6 and 14 weeks after inoculation in the laboratory trial:

| Intervals (Depth Into Log From End) | Percent Sapwood Colonized After Time | |
|---|---|---|
| (cm) | Six Weeks | Fourteen Weeks |
| 0.0-2.5 | 65 | 66 |
| 2.6-5.1 | 59 | 57 |
| 5.2-7.6 | 13 | 43 |
| 7.7-10.2 | 0 | 27 |
| 10.3-15.2 | 0 | 19 |

Treatments with D97 inoculated 2 or 4 weeks before wild type *O. piliferum, O. piceae,* or *O. minus,* resulted in 48% to 76% of the sapwood colonized by D97 (Table 2, below). These values are closely related to the percent of sapwood colonized in treatments with D97 alone, Table 1, above. Results showed a significant difference between D97 treated before wild type *O. piliferum, O. piceae,* and *O. minus* and D97 treated after each of these fungi.

Inoculation of D97 simultaneously with *O. piliferum, O. piceae,* or *O. minus,* resulted in D97 colonization percentages of 50, 36 and 43, respectively (Table 2). Inoculation of D97 simultaneous with these fungi, in comparison to inoculation of D97 before these fungi, resulted in lower colonization percentages of D97 when simultaneously inoculated (Table 2).

Inoculation of wild type *O. piliferum* to log ends two weeks prior to D97 resulted in exclusion of D97 (0%) from the sapwood (Table 2). D97 colonized 19% of the sapwood when inoculated 2 weeks after *O. minus.*

TABLE 2

Percent of sapwood in treatments colonized by D97, when D97 is inoculated after, simultaneously, or before other fungi in the laboratory:

TABLE 2

Percent of sapwood in treatments colonized by D97, when D97 is inoculated after, simultaneously, or before other fungi in the laboratory:

| | Percent Sapwood Colonized By D97 | | |
|---|---|---|---|
| Inoculation of logs with D97 | *O. piliferum* | *O. piceae* | *O. minus* |
| 2 wks after | 0 | 6 | 19 |
| simultaneously | 50 | 36 | 43 |
| 2 wks before | 62 | 58 | 66 |
| 4 wks before | 76 | 58 | 55 |

Individual inoculation of log ends with wild type *O. piliferum, O. piceae,* or *O. minus,* resulted in sapwood colonization percentages of 77, 44 and 38, respectively for each fungus (Table 3, below). Average laboratory colonization rates for wild type blue stain fungi were 7.3, 5.0, and 5.9 mm/wk for *O. piliferum, O. piceae* and *O. minus.* Variations in the fungal colonization and growth rate of these fungi were observed at the genus and species levels.

The percent sapwood colonized by blue stain fungi when inoculated two weeks after D97 is 0% (Table 3). Exclusion of *O. minus* is also observed when inoculation of D97 occurs four weeks prior to such fungus. Inoculation of *O. piliferum* and *O. piceae* to log end 4 weeks after D97, resulted in colonization percentages for *O. piliferum* and *O. piceae* of 1% and 10%, respectively (Table 3). Sapwood that was colonized by *O. piliferum* and *O. piceae* occurred in only 1 of 4 logs sampled for each treatment. Results show no significant difference between D97 treatments when inoculated 2 weeks before *O. piliferum, O. piceae* or *O. minus,* and when inoculated 4 weeks before these fungi (Table 3). A significant difference was observed between D97 treatments inoculated prior to *O. piliferum, O. piceae,* and *O. minus* and individually inoculated treatments (Table 3).

Simultaneous inoculation of logs with the wild type fungi and D97 resulted in sapwood colonization of 53, 22, and 0% for O. piliferum, 0. piceae, and O. minus, respectively (Table 3).

Colonization of sapwood by wild type *O. piliferum, O. piceae,* or *O. minus,* resulted in 56, 55 and 19, colonization, respectively, when inoculated 2 weeks before D97 (Table 3). Significant colonization of the sapwood was obtained by all species when inoculated before D97, except the *O. minus* treatment that colonized only 19% of the sapwood.

TABLE 3

Percent of sapwood in treatments colonized by wild type *Ophiostoma piliferum, O. piceae,* and *O. minus,* when Carlapip is inoculated after, simultaneously, or before these fungi in the laboratory:

TABLE 3

Percent of sapwood in treatments colonized by wild type *Ophiostoma piliferum, O. piceae,* and *O. minus,* when Cartapip is inoculated after, simultaneously, or before these fungi in the laboratory:

| | Percent Sapwood Colonized By Blue Staining | | |
|---|---|---|---|
| Inoculation of logs with D97 | *O. piliferum* | *O. piceae* | *O. minus* |
| 2 wks after | 56 | 55 | 19 |
| simultaneously | 53 | 22 | 0 |
| 2 wks before | 0 | 0 | 0 |
| 4 wks before | 1 | 10 | 0 |
| Control[z] | 77 | 44 | 38 |

[z]Control = inoculation of logs with the wild type Ophiostoma spp. and not challenged by D97.

EXAMPLE 1A

Following the procedure of Example 1, the pitch-degrading white rot fungus *Phanerochaete gigantea* (NRRL 21054) is evaluated in the place of the D97 fungus. In this study, *O. minus* was omitted as was the inoculation of NRRL 21054 two weeks after inoculation with the blue staining fungi. Results indicated essentially the same ability of *Phanerochaete gigantea* to protect the wood against the staining fungi as is shown for D97 in Tables 2 and 3, above.

EXAMPLE 2

A field study was conducted in June at the Cloquet Forestry Center, Cloquet Minn., using plots located in the southwest corner of the station (T - 49, R - 18, section 36). The site was located between a 2 year old clear cut area and a mature red pine plantation. Red pine trees, approximately 60 to 70 years old with an average diameter of 20.3 cm, were felled and cut into lengths of approximately 61 cm. Logs were inoculated 1 to 2 days after cutting.

Treatments consisted of a water control, an anti-transpirant, D97 at a concentration of $5.1\times10^7$ CFU/ml with an anti-transpirant, D97 treatment at $5.1\times10^7$ CFU/ml, and D97 at $5.1\times10^6$ CFU/ml. The anti-transpirant used to retain moisture of the log surfaces was Foreevergreen® (Mycogen Corporation, San Diego Calif.). Forevergreen® treatments consisted of 202 ml diluted with 1420 ml water.

D97 was added to 1420 ml of distilled water, mixed, and sprayed with a hand sprayer with a pressure of 30–40 p.s.i. Each log was individually sprayed including bark and sawn ends until slight runoff. The thirteen inoculated logs were then piled into a pyramidal shape. The anti-transpirant treatments were inoculated immediately after the D97 inoculation or water used for control treatments.

Logs were sampled 4 weeks after inoculation by cutting lengths of approximately 20.3 cm from 2 logs per treatment. Isolations were made from the logs as described in Example 1, except for a difference in the selective medium used. The selective media for Ophiostoma was modified slightly from that used by Harrington in "Cycloheximide Sensitivity As A Taxonomic Character In Ceratocystis, Mycologia", 72, 1123–1129, 1981 (0.01 g/l cycloheximide and 0.01 g/l streptomycin sulfate). Colonization percentages were calculated from the total number of isolation attempts obtained per log (12 chips/log), within 2.5 cm of the log end.

Additional D97 treatments including, D97 at $5.1\times10^6$ CFU, D97 at $5.1\times10^7$ CFU and D97 with an anti-transpirant, were added in order to examine the effect that inoculation time had on sapwood colonization by D97 and blue stain fungi. Inoculation of logs occurred 1 to 2 days, 2 weeks and 4 weeks after cutting. Sampling and analysis of logs occurred as listed above, see Example A and Table 5, below.

Visual observations of fungal growth on log ends in the above field study showed good colonization by D97 at 2 weeks after inoculation. The percent of sapwood colonized by D97 in treated logs was 100, 100, and 92% for treatments of D97 at $5.1\times10^6$ CFU, D97 at $5.1\times10^7$ CFU and D97 with an anti-transpirant, respectively (Table 4). A significant difference was observed between D97 treated and untreated logs, but no significant difference was observed between any of the D97 treated logs, see Table 4, below. The growth of D97 on the bark of logs was not observed, and attempts to isolate D97 from the bark were unsuccessful. Colonization of blue stain fungi from the sapwood yielded percentages of 63, 63, 0, 8, and 8% for control, anti-transpirant alone, D97 at $5.1\times10^6$, D97 at $5.1\times10^7$, and D97 with anti-transpirant treatment, respectively (Table 4). A significant difference in colonization of blue stain fungi, was observed between treated and untreated logs.

EXAMPLE 3

A second field study was initiated in late August. Treatments consisted of those described for the first field study (Example 2), but with the ($5.1\times10^6$ CFU/ml) D97 treatment deleted. Sampling of logs also occurred as described above, with an additional log assayed at each sampling time. Colonization percentages were calculated from the total number of isolation attempts obtained per log (8 chips/log), within 1.90 cm of the log end.

Each log per treatment in the laboratory trial was considered a replicate (block), therefore the data was analyzed as a complete randomized block design. Each log in field treatments was also evaluated as a replicate, and results averaged. Visual observations of logs in the second field study showed similar results. Colonization of the sapwood by D97 yielded 4, 0, 96, and 96% for control, anti-transpirant, D97 at $5.1\times10^7$, and D97 with anti-transpirant treatments, see Table 4, below. Statistical analysis of the results, showed a significant difference between treated and untreated logs. The percent sapwood colonized by blue stain fungi was 29, 71, 0, and 4% for control, anti-transpirant, D97 ($5.1\times10^7$), and D97 with an anti-transpirant (Table 4). No significant difference was observed between control logs and D97 treated logs, but a significant difference was observed between anti-transpirant and D97 treated logs.

TABLE 4

Percent of sapwood in field study treatments (logs inoculated 1 to 2 days after cutting) colonized by D97 and/or blue stain fungi, at 4 weeks after inoculation:

| | Field Study One (Example 2) | | Field Study Two (Example 3) | |
|---|---|---|---|---|
| Treatments | D97 | Wild Type Blue Stain Fungi | D97 | Wild Type Blue Stain Fungi |
| Control | 0 | 63 | 4 | 29 |
| Anti-transpirant | 0 | 63 | 0 | 71 |
| D97 ($5.1\times10^6$)/ml | 100 | 0 | — | — |
| D97 ($5.1\times10^7$)/ml | 100 | 8 | 96 | 0 |
| D97 with Anti-transpirant | 92 | 8 | 96 | 4 |

EXAMPLE 4

Data from the field studies as above described were analyzed relative to colonization effects relative to time of treatment after cutting of the trees. Percent sapwood colonized was determined when inoculations took place 1–2 days after falling off the trees, 2 weeks after falling and 4 weeks after the falling, with blue stain fungi (wild type O. piliferum, *O. piceae* and O. minus) being inoculated over D97 4 weeks after cutting.

As seen in Table 5, below, results showed colonization percentages of blue stain fungi increase as the time of inoculation increased from 1–2 days to 4 weeks after cutting. Colonization percentages increased for blue stain fungi from 0 to 33%, 8 to 50%, and 8 to 29% for treatments of D97 ($5.1\times10^6$), D97 ($5.1\times10^7$) and D97 with an anti-transpirant, respectively. In general, D97 colonization percentages decreased as the inoculation time increased from 1–2 days to 4 weeks after cutting. D97 percentages decreased from 100 to 54%, 100 to 42%, and 96 to 38% for treatments D97 ($5.1\times10^6$), D97 ($5.1\times10^7$ with an anti-transpirant, respectively. Greatest inhibition of blue stain fungi and maximum colonization of D97 in sapwood was obtained when inoculation occurred 1 to 2 days after cutting.

The fungi used in this invention are indicated to grow white and/or colorless. Fungi such as white rot fungi generally grow largely or essentially white. However, fungi such as Ophiostoma and members of the class to which it belongs may grow white or have white portions, but also may have substantial colorless portions and may even grow essentially colorless, not only at the surface, but particularly within wood which they penetrate. When growing colorless, detection is often not readily ascertained and close examination may be required. Any white residue left by any fungi used herein is usually minor and in any event is not considered a stain for purposes of this invention. However, fungi of the classes Ascomycetes and Deuteromycetes which grow largely or essentially colorless can be preferred aesthetically for use herein for such colorless growth.

What is claimed is:

1. A method of reducing the amount of color staining caused by wood staining fungi on logs to be cut into structural wood comprising inoculating the ends of a log to be cut into structural wood with an amount of at least one fungus of the class Basidiomycetes effective to reduce the amount of color staining caused by the wood staining fungi and which grows white and/or colorless and which reduces the pitch content of the wood, allowing the at least one white and/or colorless fungus to grow on and into the log ends to thereby reduce the amount of color staining caused by the wood staining fungi and thereafter cutting the log into structural wood.

2. The method of claim 1 in which the Basidiomycetes is selected from the group consisting of *Schizophyllum commune, Tricaptum biforme, Phanerochaete gigantea* and *Phlebia tremellosa.*

3. The method of claim 1 in which the log ends are inoculated with the white and/or colorless pitch content-reducing fungus in conjunction with an anti-transpirant.

4. The method of claim 1 in which the log is treated with an effective amount of an insecticide against bark beetles.

5. The method of claim 1 in which the log ends are inoculated with the white and/or colorless, pitch content-reducing fungus in conjunction with an adjuvant.

6. The method of claim 1 in which the adjuvant is carboxymethylcellulose.

7. The method of claim 1 in which the log to be cut into structural wood is debarked prior to inoculation and the debarked surfaces are thereafter treated with an amount of at least one fungus effective to reduce the amount of color staining caused by the wood staining fungi and which grows white and/or colorless.

8. The method of claim 1 in which the log ends are inoculated in no more than two days after cutting of the tree from which the log is obtained.

9. The method of claim 1 in which the wood is pure wood.

10. A method of reducing the amount of color staining caused by wood staining fungi on structural wood comprising inoculating at least 60% of the surface area of the

TABLE 5

| | D97 | | | Blue Stain Fungi | | |
|---|---|---|---|---|---|---|
| Time of inoculation after cutting | ($5.1\times10^6$) | ($5.1\times10^7$) | (Cart. w/ anti-tran.) | ($5.1\times10^6$) | ($5.1\times10^7$) | (Cart. w/ anti-tran.) |
| 1 to 2 days | 100 | 100 | 92 | 0 | 8 | 8 |
| 2 weeks | 100 | 92 | 96 | 17 | 21 | 8 |
| 4 weeks | 54 | 42 | 38 | 33 | 50 | 29 |

structural wood with an amount of at least one fungus of the class Basidiomycetes effective to reduce the amount of color staining caused by the wood staining fungi and which grows white and/or colorless and which reduces the pitch content of the wood, and allowing the at least one white and/or colorless fungus to grow on and into the structural wood to thereby reduce the amount of color staining caused by the wood staining fungi.

11. The method of claim 10 in which the white and/or colorless, pitch content-reducing fungus is inoculated onto the structural wood in no more than one week after cutting of the structural wood from its log source.

12. A method of reducing the amount of color staining caused by wood staining fungi on wood chips to be converted into pulp comprising inoculating the wood chips to be converted into pulp with an amount of at least one fungus of the class Basidiomycetes effective to reduce the color staining caused by the wood staining fungi and which grows white and/or colorless and which reduces the pitch content of the wood, allowing the at least one white and/or colorless fungus to grow on the wood chips to thereby reduce the amount of color staining caused by the wood staining fungi and thereafter converting the wood chips to pulp.

13. The method of claim 12 in wherein the white and/or colorless growing Basidiomycetes fungus is selected from the group consisting of *Schizophyllum commune, Trichaptum biforme, Phanerochaete gigantea* and *Phlebia tremellosa.*

* * * * *